United States Patent [19]

Sakamoto et al.

[11] Patent Number: 5,432,279
[45] Date of Patent: Jul. 11, 1995

[54] PROCESS FOR THE PREPARATION OF BINARY INDOLE ALKALOIDS

[75] Inventors: Naoya Sakamoto; Hiroaki Tan; Eiichirou Hata; Noriaki Kihara, all of Yamaguchi, Japan

[73] Assignee: Mitsui Petrochemical Industries, Inc., Tokyo, Japan

[21] Appl. No.: 55,788

[22] Filed: May 3, 1993

Related U.S. Application Data

[63] Continuation of Ser. No. 768,451, Aug. 30, 1991, abandoned, which is a continuation-in-part of Ser. No. 484,562, Feb. 26, 1990, abandoned.

[30] Foreign Application Priority Data

| Mar. 4, 1989 | [JP] | Japan | 1-50988 |
| Mar. 4, 1989 | [JP] | Japan | 1-50989 |
| Mar. 4, 1989 | [JP] | Japan | 1-50990 |
| Mar. 4, 1989 | [JP] | Japan | 1-50991 |
| Jul. 28, 1989 | [JP] | Japan | 1-194306 |
| Sep. 8, 1989 | [JP] | Japan | 1-231659 |
| Nov. 2, 1989 | [JP] | Japan | 1-284966 |

[51] Int. Cl.⁶ ........................ C07D 519/04
[52] U.S. Cl. ........................ 540/478
[58] Field of Search ........................ 540/478

[56] References Cited

U.S. PATENT DOCUMENTS

5,037,977  8/1991  Tan et al. ........................ 540/478

FOREIGN PATENT DOCUMENTS

3801450  8/1988  Germany ........................ 540/478
2204036  11/1988  United Kingdom ........................ 540/478
2215331  9/1989  United Kingdom ........................ 540/478

OTHER PUBLICATIONS

Chemical Abstracts 9th Collective Index, Chemical Substances, p. 40240 (1974).
Cullman, Chem Abs 82, 57996b (1974).
Grant & Hackh's Chemical Dictionary, 5th Et p. 30 (1987).
Encyclopedia of Technology, 3rd ed. Hampel, Ed (1990) p. 62.
Random House Dictionary, 2nd Edition (1988).
Hackh's Dictionary, 3rd Edition (1964) p. 44.

*Primary Examiner*—Mark L. Berch
*Attorney, Agent, or Firm*—Nixon & Vanderhye

[57] ABSTRACT

The present invention relates to a process for the preparation, from e.g. anhydrovinblastine, of binary indole alkaloids effective as an anti-cancer drug, such as vinblastine, leurosidine, etc., wherein a trivalent iron source and hydride source are added in the presence of oxygen, thereby increasing a yield of an object compound. The yield of an object compound is improved still more by further addition, to the reaction system, of an oxalic acid ion source, malonic acid ion source, inorganic anion source, amino acid, etc.

16 Claims, No Drawings

PROCESS FOR THE PREPARATION OF BINARY INDOLE ALKALOIDS

This is a continuation of application Ser. No. 07/768,451, filed Aug. 30, 1991, now abandoned, which is a continuation-in-part of Ser. No. 07/484,562, filed Feb. 26, 1990 now abandoned.

BACKGROUND OF THE INVENTION

The present invention relates to a process for the preparation of binary indole alkaloids, such as vinblastine or leurosidine, which are effective as an anti-cancer drug.

Conventional processes for the preparations, e.g. through chemical transformation of 3', 4'-anhydrovinblastine (AVLB), of binary indole alkaloids possessing an anti-tumor activity, such as vinblastine (VLB) and leurosidine (LEU) include e.g. the process disclosed in J. C. S. Chem. Commn. 583, 1979. However, the yields of object vinblastine (VLB) and leurosidine (LBU), etc., are very poor as low as 1 to 2%. Also, the processes employing an enzyme are disclosed in J. C. S. Chem. Commn. 257, 1979 and Phytochemistry 26(12), 3233 (1987). In these processes, however, there are disadvantages, such as very low yields, long reaction times, etc. Thus, both processes had problems for industrial production and were not satisfactory processes.

SUMMARY OF THE INVENTION

The problem to be solved by the present invention resides in solving the problems of the above conventional methods, and the object of this invention is to provide an industrially advantageous process for the preparation, where binary indole alkaloids, which are effective as an anti-cancer drug, such as vinblastine, leurosidine, or the like, can be prepared in a higher yield.

For accomplishment, of the above object, the present inventors employs 3', 4'-anhydrovinblastine (referred to as AVLB, hereinafter) as a starting material and attempted several types of hydration reactions, redox reactions, etc. As a result, they have found that vinblastine (referred to as VLB, hereinafter), leurosidine (referred to as LEU, hereinafter), etc., which are effective as an anti-cancer drug, can be synthesized from AVLB in one step in a higher yield, by the addition of a hydride source to a solution containing AVLB in the presence of trivalent iron and oxygen.

Furthermore, the inventors have found that the presence of water results in a higher conversion and yield which would not be expected from the teachings of the art (for example, Kutney et al., British Patent Nos. 2,204,036 and 2,215,331 which direct the reader to use exclusively organic solvents in non-aqueous systems. There is no suggestion of using aqueous systems in the art.

In addition, the method described by Kutney et al. in British Patent No. 2,215,331 employs the enamine (formula VIII, page 23) as a starting material which contains 3', 4'-anhydrovinblastine(AVLB) as an impurity, whereas the present invention utilizes pure AVLB which can be obtained, for example, by reacting catharanthine with vindoline according to the method as described in U.S. Pat. No. 4,778,885, or U.S. Pat. Ser. No. 07/390,903 now U.S. Pat. No. 5,037,977, or by the extraction from *Catharanthus roseus*, or by the reduction of an iminium compound with sodium borohydride, which compound can be obtained from catharanthine N-oxide which was obtained by oxidation of catharanthine, and vindoline by the method described in Example 1 of British Patent No. 2,204,036. The enamine used in British Patent No. 2,215,331 as the starting material must be prepared from an iminium compound using expensive dihydronicotinamide as described in the Example. Thus, the method of the present invention has also a technical advantage over the method as disclosed in British Patent No. 2,204,036 and could not easily been suggested by it.

That is, the present invention relates to a process for the preparation of a compound represented by the formula(II):

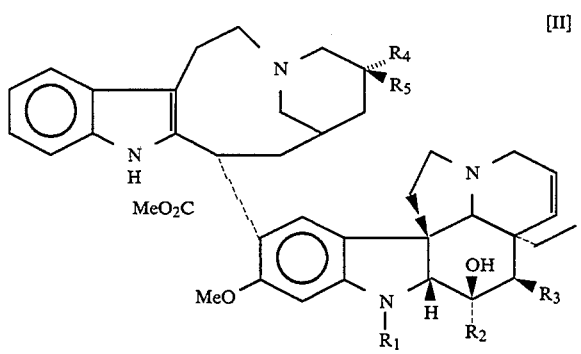

where $R_1$ represents a hydrogen atom, a lower alkyl group or formyl group, $R_2$ is a lower alkoxy-carbonyl group or amide group, $R_3$ is an acetoxy group or hydroxy group and $R_4$ is a hydroxy group and $R_5$ is and ethyl group, or $R_4$ is an ethyl group and $R_5$ is a hydoroxy group, comprising the step of:

(1) dissolving in an aqueous reaction medium containing at least 80% by volume of water a compound of the formula (I):

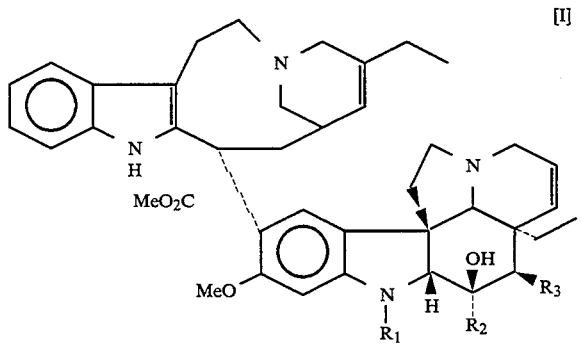

where $R_1$, $R_2$ and $R_3$ are as defined above or a salt thereof, a source of reactive trivalent iron soluble in the reaction medium and selected from ferric chloride, ferric sulfate and ferric nitrate;

(2) dissolving sxygen in the reaction medium;

(3) adding a hydride source, selected from sodium borohydride, potassium borohydride or sodium borocyanohydride, to the oxygen-contaioning reaction medium; and thereafter (4) recovering the compound of formula (II) from the reaction medium.

According to the present invention, VLB as shown below by the formula (V) (wherein $R_1$ denotes a hydroxy group, and $R_2$ denotes an ethyl group) and LEU (formula (V) wherein $R_1$ denotes an ethyl group, and R₂ denotes a hydroxy group) can be prepared from AVLB of the formula (IV) as a starting material. Other compounds of the above formula (II) wherein $R_1$ is a hydrogen atom, including e.g. N-des methylvinblastine, and a compund of the formula (II) wherein $R_1$ is a formyl group including e.g. vincristine, can be synthesized from corresponding compound of formula (I) as a starting material.

An oxygen source may be oxygen or inert gas-diluted oxygen, but normally, air is preferred. For one of preferable processes, an oxygen-containing gas is bubbled through a reaction solution for a determined time so as to dissolve an suitable amount of oxygen in the reaction solvent, prior to the addition of the hydride source.

As the reaction temperature, a wide range from a melting point of reaction solvent to approx. 50° C., preferably −20 to 10° C., can be adopted.

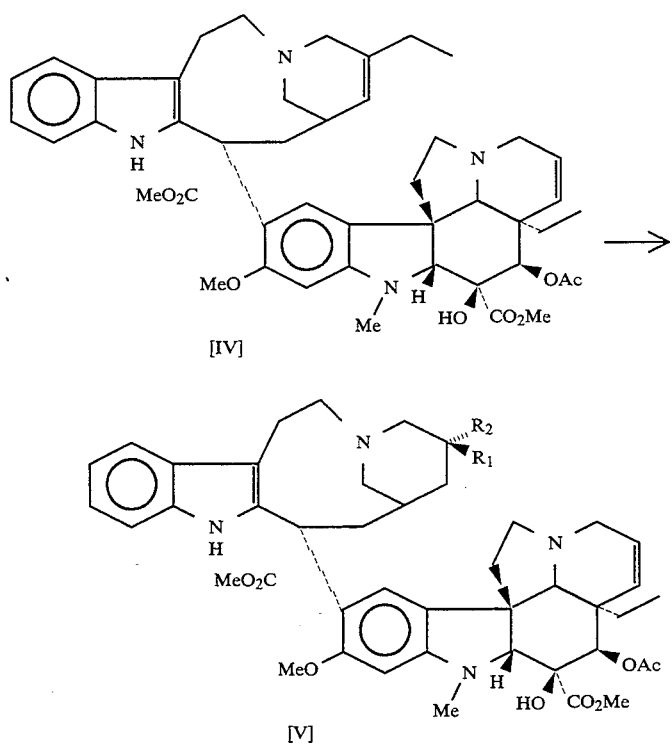

DETAILED DESCRIPTION OF THE INVENTION

The present invention can be carried out in a very simple process in which a hydride source is added to a suitable solvent dissolving a trivalent iron source and a compound or a salt thereof represented by the general formula (I), in the presence of oxygen.

The trivalent iron to be employed may be any if it can be dissolved in the reaction mixture and participate in the reaction. In particular, chlorides, sulfates, and nitrates are preferable. The amount of these to be added is 0.01 to 10,000-fold molar excess, preferably 1 to 2,000-fold molar excess, based on the starting material.

Solvents which may be mentioned are aqueous media containing at least 80% by volume of water. Examples of solvents to be used with water are alcohols such as methanol, ethanol, etc., THF, acetonitrile, DMF, DMSO, etc.

A mixture of 2 or more of these solvents may also be employed. Preferably employed is H₂O alone, or a H₂O-methanol mixture containing at least 80% by volume of H₂O.

Hydride sources to be added can include sodium borohydride, potassium borohydride, sodium borocyanohydride, and amine complexes of borane. The hydride source is added in a amount of 0.05 to 10-fold molar excess, preferably 0.1 to 5-fold molar excess, based on the trivalent iron.

In the process for the preparation according to the present invention, further addition of (i) an oxalic acid ion source and/or a malonic acid ion source, (ii) an inorganic anion source, or (iii) an amino acid can further raise the yield of an object compound. Also, in the case of the above described (i), (a) it is further preferred to add a dicarboxylic acid or a salt thereof represented by the general formula (III), and further addition of amino acid thereto is more preferable, or

(III)

(wherein $R_7$ and $R_9$, stand for a hydrogen atom or a lower alkyl group, $R_6$ and $R_8$ stand for a hydrogen atom or a lower alkyl group, or together form a double bond), (b) it is preferred to add pyridine or its derivative, and further addition of amino acid thereto is more preferable, or (c) it is preferred to add inorganic anion, and further addition of amino acid thereto is more preferable, or (d) addition of amino acid is preferable. In the case of the above descrived (ii) further addition of amino acid is preferable.

The sources of oxalic acid ion and malonic acid ion can be any of ones if it can be dissolved in the reaction solvent, to form a complex with the trivalent ion. In the cases of the addition of free oxalic acid and malonic acid, however, it is necessary to add further a suitable base in an equivalent amount to those of free acid. Preferable examples of oxalic acid ion sources for the addition can include, as the type of a salt, alkali metal salts, such as an Li salt, Na salt, K salt, etc., an ammonium salt, and an alkyl ammonium salt. These are added in an amount of 0.1 to 10-fold molar excess, preferably 1 to 4-fold molar excess, based on the trivalent iron. Also, the addition of a previously prepared complex salt of trivalent iron-oxalic acid and/or a complex salt of trivalent iron-malonic acid is one of the preferable processes, as the simultaneous addition of an oxalic acid source and/or a malonic acid source and a trivalent iron source. The complex salts of trivalent ion-oxalic acid can be exemplified as e.g. $(NH_4)_3$ $Fe(C_2O_4)_3$, $K_3Fe(C_2O_4)_3$, etc., and the complex salts of malonic acid salts can include e.g. $(NH_4)_3$ $Fe(C_3O_4)_3$, $K_3Fe$ $(C_3H_2O_4)_3$, etc.

The inorganic anion sources are not particularly restricted. However, inorganic anions like $CO_3^{2-}$ and $PO_4^{3-}$—which from insoluble iron salts—are excluded. In the present invention, particularly preferred are $Cl^-$, $Br^-$, $I^-$, $SO_4^{2-}$, etc. The type of a salt of an inorganic anion source can be any of ones if they can be dissolved in the reaction solvent. In particular, an ammonium salt, an alkylammonium salt, and an alkali metal salt are preferred. An addition amount of these is 0.1 to 100-fold molar excess, preferably 1 to 10-fold molar excess, based on the trivalent iron.

The amino acid can be any of amino acids, but preferable are the ones of a lower molecular weight, such as glycine, etc. More preferable are glycine and N-methlglycine. Its addition amount is 0.01 to 1,000-fold molar excess, preferably 1 to 10-mold molar excess, based on the trivalent iron.

The compounds represented by the formula (III) include maleic acid, citraconic acid, succinic acid, itaconic acid, etc., however, they are not restricted to these exemplified compounds. In particular, maleic acid and succinic acid can be cited as preferable examples.

It is preferred that these compounds are added especially in the form of salts. The type of a salt may be any, though particularly preferred are an ammonium salt and an alkyl ammonium salt. In the case where a free salt is added, it is required to further add a suitable salt base in an equivalent amount to free acids or so. They are added in amount of 0.1 to 3-fold molar excess, preferably 0.3 to 2-fold molar excess, based on the trivalent iron.

Pyridine or its derivatives include pyridine derivatives, such as phridine, alkylpyridine, etc., $\alpha$, $\alpha'$-bipyridyl derivatives, such as $\alpha$, $\alpha'$-bipyridyl, alkyl $\alpha$, $\alpha'$-bipyridyl, etc. In particular, $\alpha$, $\alpha'$-bipyridyl is preferable. Its addition amount is 0.01 to 10-fold molar excess, preferably 0.1 to 3-fold molar excess, based on the trivalent iron.

The process for the preparation according to the present invention can ba made continuous by a allowing the respective compounds of (I) type compound, a hydride source, oxygen, and a trivalent iron to be included in two or more solutions, and then by allowing said two or more solutions to continuously contact with each other, or more preferably by allowing allowing an oxygen- and trivalent iron- and (I) type compound-containing solution to continuously contact with a hydride source-contacting solution.

This continuous process for the preparation can be carried out in a very simple operation in which e.g. the above-described two or more solutions are simultaneously and continuously fed into the inlet of one end of a reaction column, to be allowed to contact and mix with each other, whereby the reaction is completed while the solutions are past through the column, so that the reaction mixture is continuously recovered from outlet of another side of the column.

The yield of an object compound can be significantly increased by addition of one or more components selected from a pyridine derivative, an inorganic anion source, a dicarboxylic acid or salt thereof represented by the formula (III), and an amino acid, together with an oxalic acid source and/or malonic acid source, to any solution to be contacted and mixed in this continuous process.

Usually, these addition components are most preferably added to a solution which contains a trivalent iron source.

To this, however, the addition method is not restricted. The yield is increased, almost similarly as above, by addition of the components to any of two or more solutions to be contacted.

However, the addition of a combination by which the hydride source is rapidly degraded should be avoided.

The pyridine derivatives may be any if those are a phridine derivatives. Particularly preferred are pyridine, alkylphridines, $\alpha$, $\alpha'$-bipyridine, alkyl $\alpha$, $\alpha'$-bipyridines. Its addition amount is 0.01 to 10-fold molar excess based on the trivalent iron.

It is preferable than an oxygen source is suitably dissolved in any of the solutions to be contacted, by previously bubbling an oxygen-containing gas.

Contact time for the reaction solutions is 0.1 sec. to 60 min., preferably 1 sec. to 10 min.

The reaction vessel may be any shapes; a column-shaped reaction vessel is particularly preferred.

As compared with conventional processes, the process according to the present invention has the advantages that vinblastine (VLB), leurosidine (LEU), etc. —which are effective as an anti-cancer drug—can be obtained e.g. from 3'4'-anhydrovinblastine (AVLB), in a higher yield and easier operation.

Taking into consideration that vinblastine (VLB) is a very high-priced anti-cancer drug, the effects brought by the present invention are extremely high.

EXAMPLES

The present invention is further illustrated below. The present invention should not be construed as being limited by the Examples.

EXAMPLE 1

To a 50 ml-reaction vessel were put 10 ml of $H_2O$, 1.9 mg of AVLB, 1 ml of an aqueous solution of $FeCl_3 \cdot 6H_2O$ (1.2M), and 0.024 ml of an aqueous solution of 2N HCl, and the mixture was stirred for 30 min. under cooling with ice while air was bubbled. Following addition of 1 ml of an aqueous solution of $NaBH_4$(0.227M), the mixture was stirred for an additional 30 min. Then, 2 ml of 25% ammonia water was added, whereby the solution was made basic. The products were extracted by addition of 10 ml of ethyl acetate, 3 times. The extracts were combined and evaporated to dryness under reduced pressure at 40° C. or less. The resulting sample was analyzed by high-performance liquid chromatography (HPLC) under the conditions described below. At this time, the conversion rate of AVLB was 95%, the yield of VLB was 10%, and the yield of LEU was 6%.
(Analytical Conditions)

Column: YMC-packed column A-512(CN) 6×150 mm
Mobile phase: $H_2O$: MeOH:Et$_3$N:AcOH=1500:1500:4:1.6
(V/V/V/V)

Flow rate: 1 ml/min
Column temperature: 45°
Detection: UV (254 nm)

| Retention time: | VLB | 19.5 min |
|---|---|---|
| | LEU | 17 min |
| | AVLB | 46 min |

Examples 2 to 4

The procedure was carried out in the same manner as in Example 1 except that glycine was further added in a predetermined amount. The results are shown in Table 1.

TABLE 1

| Example | Glycine/Fe$^{3+}$ (Molar ratio) | Conversion rate of AVLB (%) | Yield of VLB (%) | Yield of LEU (%) |
|---|---|---|---|---|
| 2 | 2 | 90 | 15 | 10 |
| 3 | 4 | 87 | 21 | 12 |
| 4 | 5 | 85 | 14 | 9 |

Example 5

The procedure was carried out in the same manner as in Example 3 except that glycine in Example 3 was replaced by N-methylglycine. At this time, the conversion rate of AVLB was 66%, the yield of VLB was 24%, and the yield of LEU was 14%.

Examples 6 to 8

The procedure was carried out in the same manner as in the same manner as in Example 3 except that the amount of Fe$^{3+}$ and NaBH$_4$ in Example 3 were varied. The results are shown in Table 2.

TABLE 2

| Example | Amount of Fe$^{3+}$ soln. (ml) | Amount of NaBH$_4$ soln. (ml) | Conversion rate of AVLB (%) | Yield of VLB (%) | Yield of LEU (%) |
|---|---|---|---|---|---|
| 6 | 0.4 | 0.4 | 32 | 7 | 3 |
| 7 | 0.5 | 0.5 | 35 | 9 | 4 |
| 8 | 2 | 2 | 69 | 16.5 | 9 |

Examples 9 to 11

The procedure was carried out in the same manner as in Example 3 except that the amount of NaBH$_4$ in Example 3 was varied, The results are shown in Table 3.

TABLE 3

| Example | Amount of NaBH$_4$ soln. (ml) | Conversion rate of AVLB (%) | Yield of VLB (%) | Yield of LEU (%) |
|---|---|---|---|---|
| 9 | 0.5 | 29 | 10.5 | 6 |
| 10 | 2 | 69 | 11.5 | 7 |
| 11 | 5 | 91 | 16 | 9 |

Examples 12 to 14

The procedure was carried out in the same manner as in Example 3 except that the FeCL$_3$. 6H$_2$O solution in Example 3 was replaced by other iron sald solutions. The results are shown in Table 4.

TABLE 4

| Example | Iron salt | Conversion rate of AVLB (%) | Yield of VLB (%) | Yield of LEU (%) |
|---|---|---|---|---|
| 12 | Fe(NO$_3$)$_3$.9H$_2$O | 20 | 4 | 2 |
| 13 | Fe$_2$(SO$_4$)$_3$ | 75 | 18 | 11 |
| 14 | FeBr$_3$ | 26.5 | 4 | 1 |

Examples 15 to 16

The procedure was carried out in the same manner as in Example 3 except that NaBH$_4$ in example 3 was replaced by other hydride sources. The results are shown in Table 5.

TABLE 5

| Example | Hydride source | Conversion rate of AVLB (%) | Yield of VLB (%) | Yield of LEU (%) |
|---|---|---|---|---|
| 15 | NaBH$_3$CN | 80 | 14 | 10 |
| 16 | NBH$_4$ | 89 | 19 | 11 |

Example 17

In a 50 ml-reaction vessel were placed 10 ml of H$_2$O, 1.9 mg of 3', 4'-anhydrovinblastine (AVLB), 500-fold molar excess (NH$_4$)$_3$Fe(C$_2$O$_4$)$_3$. 3H$_2$0 basec on AVLB, and 0.024 ml of an aqueous solution of 2N HCl. The mixture was stirred under cooling with ice over 30 min., while air was bubbled. Then, 1 ml of an aqueous solution of NaBH$_4$ (0.227M) was added, and the mixture was stirred for an additional 30 min.

The mixture was made basic by addition of 2 ml of 25% ammonia water and was extracted with 10 ml of ethyl acetate, 3 times. The extracts were combined and evaporated to dryness under reduced pressure at 40° C. or less. The products were analyzed by HPLC under the following conditions. At this time, the conversion rate of 3',4'-anhydrovinblastine (AVLB) was 97%, the yield of vinblastine (VLB) was 23%, and the yield of leurosidine (LEU) was 12%.
(Analytical Conditions)

Colmn: YMC-packed column AM-312 6×150 mm
Mobil phase: Aqueous solution of 0.01M ammonium carbonate : acetonitrile =1200:1800 (V/V)
Flow rate: 1 ml/min
Temperature: 45°
Detection wavelength: UV (254 nm)

| Retention time: | VLB | 12.3 min |
|---|---|---|
| | LEU | 9.0 min |
| | AVLB | 39.1 min |

Example 18

The procedure was carried out in the same manner as in Example 17 except that 4-fold molar excess glycine based on the iron atom in Example 17 was added. At this time, the conversion rate of AVLB was 86%, the yield of VLB was 27%, and the yield of LEU was 14%.

Example 19

The procedure was carried out in the same manner as in Example 18 except that 1 ml of an aqueous solution of FeCl$_3$ . 6H$_2$O (1.2M) was added in place of (NH$_4$)$_3$Fe(C$_2$O$_4$).3H$_2$O in Example 18 and that 3-fold molar excess (NH$_4$)$_2$.C$_2$O$_4$ based on the trivalent iron was further added. At this time, the conversion rate of AVLB was 86.5%, the yield of VLB was 34%, and the yield of LEU was 22.5%.

Examples 20 to 21

The procedure was carried out in the same manner as in Example 19 except that the addition amount of (NH$_4$)$_2$.C$_2$O$_4$ in Example 19 was varied. The results are shown in Table 6.

TABLE 6

| Example | C$_2$O$_4$$^{2-}$/Fe$^{3+}$ (Molar ratio) | Conversion rate of AVLB (%) | Yield of VLB (%) | Yield of LEU (%) |
| --- | --- | --- | --- | --- |
| 20 | 1 | 43 | 22.5 | 15 |
| 21 | 2 | 63 | 31.5 | 21.5 |

Examples 22 to 24

The procedure was carried out in the same manner as in Example 19 except that the amount of iron added was reduced to one-half and that the amount of (NH$_4$)$_2$C$_2$O$_1$ added was varied. The result are shown in Table 7.

TABLE 7

| Example | C$_2$O$_4$$^{2-}$/Fe$^{3+}$ (Molar ratio) | Conversion rate of AVLB (%) | Yield of VLB (%) | Yield of LEU (%) |
| --- | --- | --- | --- | --- |
| 22 | 1 | 43.5 | 19.5 | 17.5 |
| 23 | 2 | 56 | 30.5 | 23.5 |
| 24 | 3 | 87.5 | 27.5 | 16.5 |

Example 25

The procedure was carried out in the same manner as in Example 19 except that the aqueous solution of FeCl$_3$6H$_2$O in Example 19 was replaced by an aqueous solution of Fe(NO$_3$)$_3$9H$_2$O. The conversion rate of AVLB was 89.5%, the yield of VLB was 26%, and the yield of LEU was 15%.

Examples 26 to 28

The procedure was carried out in the same manner as in Example 19 except that the solvent was changed from H$_2$O to other mixture solvents and that the reaction temperature was varied. The results are shown in Table 8.

TABLE 8

| Example | Solvent* | Reaction temperature(°C.) | Conversion rate of AVLB (%) | Yield of VLB (%) | Yield of LEU (%) |
| --- | --- | --- | --- | --- | --- |
| 26 | H$_2$O—MeOH | −15° C. | 74.5 | 36 | 23.5 |
| 27 | H$_2$O—DMSO | −8° C. | 74 | 21 | 14 |
| 28 | H$_2$O—CH$_3$CN | −6° C. | 71 | 29.5 | 16 |

*H$_2$O: Organic solvent = 8:2(V/V)

Examples 29 to 32

The procedure was carried out in the same manner as in Example 19 except that (NH$_4$)$_4$C$_2$O$_4$ in Example 19 was replaced by other salts. The results are shown in Table 9.

TABLE 9

| Example | Amount of oxalic acid salt | Conversion rate of AVLB (%) | Yield of VLB (%) | Yield of LEU (%) |
| --- | --- | --- | --- | --- |
| 29 | K$_2$C$_2$O$_4$ | 78 | 30.5 | 22 |
| 30 | (Me$_4$N$^+$)$_2$C$_2$O$_4$ | 89.5 | 32 | 21 |
| 31 | (Et$_4$N$^+$)$_2$C$_2$O$_4$ | 55 | 21.5 | 7.5 |
| 32 | (CH$_3$N$^+$H$_3$)$_2$C$_2$O$_4$ | 82 | 36 | 26 |

Examples 32 to 34

The procedure was carried out in the same manner as in Example 19 except that (NH$_4$)$_2$C$_2$O$_4$ in Example 19 was replaced by ammonium malonate. The results are shouwn in Table 10.

TABLE 10

| Example | Conversion rate of AVLB (%) | Yield of VLB (%) | Yield of LEU (%) |
| --- | --- | --- | --- |
| 33 | 65 | 22 | 11 |
| 34 | 80 | 30 | 12 |

*After pH was adjusted to 6.6 to 6.7, an aqueous solution of NaBH$_4$ was added.

Example 35

To a 100 ml-reaction vessel equipped with a turning blade were put 22.3 mg of 3',4'-anhydrovinblastine sulfate (AVLB. H$_2$SO$_4$), 100 ml of H$_2$O, 0.2029 g of FeCl$_3$.6H$_2$O, 0.2134 g of (NH$_4$)$_2$C$_2$O$_4$. H$_2$ $_O$ 0.0874 g of maleic acid, and 25% ammonia water (0.1025 ml) equivalent to the maleic acid. The mixture was stirred at 0° C. over 30 min. in a high speed with the turning blade while air was bubbled (50 ml/min). Then, 1 ml of aqueous 0.5 M NaBH$_4$ solution was fed with a pump in 1 min. Following stirring for an additional 30 min., the solution was made basic by addition of 5 ml of 25% ammonia water. The product was extracted with 100 ml of ethyl acetate, 3 times.

The extracts were combined and dried by means of Na$_2$SO$_4$, followed by being evaporated to dryness under reduced pressure at 40° C. or less. The residues were measured up with methanol and analyzed by high performance liquid chromatography under the same conditions as in Example 17.

At this time, the conversion rate of AVLB was 94.5%, the yield of VLB was 50%, LEU was 16%, and the selectivity of VLB was 52.9%.

Example 36

The procedure was carried out in the same manner as in Example 35 except that neither maleic acid nor ammonia water was added. At this time, the conversion rate of AVLB was 93.5%, the yield of VLB was 40%, the yield of LEU was 15. 5%, and the VLB selectively was 42.8%. Examples 37 to 40

The procedure was carried out in the same manner as in Example 35 except that the addition amounts of maleic acid and ammonia water were varied. The results are shown in Table 11.

TABLE 11

| Example | Maleic acid/Fe$^{3+}$ (mol/mol) | Conversion rate of AVLB (%) | Yield of VLB (%) | Yield of LEU (%) | VLB selectivity (%) |
| --- | --- | --- | --- | --- | --- |
| 36 | 0 | 93.5 | 40 | 15.5 | 42.8 |
| 37 | 0.5 | 90 | 42.5 | 13 | 47.2 |
| 38 | 0.75 | 88.5 | 47.5 | 14 | 53.7 |
| 39 | 1.5 | 87.5 | 49 | 10.5 | 56 |

TABLE 11-continued

| Example | Maleic acid/$Fe^{3+}$ (mol/mol) | Conversion rate of AVLB (%) | Yield of VLB (%) | Yield of LEU (%) | VLB selectivity (%) |
|---|---|---|---|---|---|
| 40 | 2 | 81 | 40.5 | 10 | 50 |

$NH_3$ water was added in amount equivalent to the maleic acid.

Examples 41 to 43

The procedure was carried out in the same manner as in Example 35 except that maleic acid was replaced by succinic acid and the addition amount was varied. The results are shown in Table 12.

TABLE 12

| Example | Succinic acid/$Fe^{3+}$ (mol/mol) | Conversion rate of AVLB (%) | Yield of VLB (%) | Yield of LEU (%) | VLB selectivity (%) |
|---|---|---|---|---|---|
| 41 | 0.75 | 97 | 43.5 | 13.5 | 44.8 |
| 42 | 1 | 93.5 | 47 | 12 | 50.3 |
| 43 | 1.5 | 87 | 44 | 11 | 50.6 |

$NH_3$ water was added in amount equivalent to the succinic acid.

Examples 44 to 46

The procedure was carried out in the same manner as in Example 35 except that maleic acid in Example 35 was replaced by other dicarboxylic acids. The results are shown in Table 13.

TABLE 13

| Example | Dicarboxylic acid | Conversion rate of AVLB (%) | Yield of VLB (%) | Yield of LEU (%) | VLB selectivity (%) |
|---|---|---|---|---|---|
| 44 | Itaconic acid | 77.5 | 34 | 9 | 47.7 |
| 45 | Citraconic acid | 88.5 | 40 | 13 | 45.2 |
| 46 | Ketosuccinic acid | 76.5 | 34 | 12 | 45.8 |

Example 47

To a 50 ml-reaction vessel were put to 10 ml of $H_2O$, 1.9 mg of AVLB, 1 ml of aqueous solution of $3FeCl_3.6H_2O$ (1.5M), 0.024 ml of 2N HCl 4-fold molar excess glycine, 6-fold molar excess $NH_4Cl$, based on $Fe^{3+}$. Following stirring the mixture over 30 min. under cooling with ice while air was bubbled, 1 ml of an aqueous solution of $NaBH_4$ (0,227M) was added and stirred for an additional 30 min. Then, 2 ml of 25% ammonia water was added, thus making the solution basic. The product was extracted with 10 ml of ethyl acetate, 3 times. The extracts were combined and evaporated to dryness under reduced pressure at not higher than 40° C. The obtained sample was analyzed by high-performance liquid chromatography under the same conditions as in Example 1. At this time, the conversion rate of AVLB was 66.5%, the yield of VLB was 30.5%, and the yield of LEU was 14.5%.

Example 48

The procedure was carried out in the same manner as in Example 47 except that $NH_4Cl$ in Example 47 was replaces by $NH_4Br$ in Example 47. At this time, the conversion rate of AVLB was 59.5%, the yield of VLB was 22%, the yield of LEU was 12.5%.

Example 49

The procedure was carried out in the same manner as in Example 47 except that $NH_4Cl$ in Example 47 was replaces by 3-fold molar excess $(NH_4)_2SO_4$ based on $Fe^{3+}$. At this time, the conversion rate of AVLB was 75%, the yield of VLB was 28%, and the yield of LEU was 15.5%.

Examples 50 to 52

The procedure was carried out in the same manner as in Example 47 except that the addition amount of $NH_4Cl$ in Example 47 was varied. The results are shown in Table 14.

TABLE 14

| Example | $NH_4Cl/Fe^{3+}$ (Molar ratio) | Conversion rate of AVLB (%) | Yield of VLB (%) | Yield of LEU (%) |
|---|---|---|---|---|
| 50 | 2 | 63 | 26 | 17.5 |
| 51 | 4 | 71 | 31.5 | 19 |
| 52 | 8 | 81.5 | 29 | 22.5 |

Examples 53 to 55

The procedure was carried out in the same manner as in Example 47 except that $NH_4Cl$ in Example 47 was replaced by other salts. The results are shown in Table 15.

TABLE 15

| Example | Added salt | Conversion rate of AVLB (%) | Yield of VLB (%) | Yield of LEU (%) |
|---|---|---|---|---|
| 53 | $(CH_3)_4NCl$ | 69.5 | 30 | 19 |
| 54 | $(CH_3)_2NH_2Cl$ | 70 | 30.5 | 22 |
| 55 | NaCl | 67 | 23 | 12.5 |

Example 56

In a 50 ml-reaction vessel were placed 10 ml of $H_2O$, 1.9 mg of AVLB, 1 ml of an aqueous solution of $FeCl_3.6H_2O$ (1.2M), 0,024 ml of an aqueous 2N HCl and 2-fold molar excess $(NH_4)_2C_2O_4$, based on $Fe^{3+}$. The mixture was stirred over 30 min. under cooling in ice while air was bubbled. After 1 ml of an aqueous solution of $NaBH_4$ (0.227M) was added, the mixture was further stirred over 30 min. By addition of 2 ml of 25% ammonia water, the mixture solution was made basic and extracted with 10 ml of ethyl acetate, 3 times. The extracts were combined and evaporated to dryness under reduced pressure at 40° C. or less. The resulting products were analyzed by high-performance liquid chromatography under the same conditions as in Example 1. At this time, the conversion rate of AVLB was 66.0%, the yield of VLB 35.5%, and the yield of LEU was 18%.

Examples 57 to 59

The procedure was carried out in the same manner as in Example 56 except that the addition amount of $NH_4Cl$ in Example 56 was varied. The results are shown in Table 16.

TABLE 16

| Example | $NH_4Cl/Fe^{3+}$ (Molar ratio) | Conversion rate of AVLB (%) | Yield of VLB (%) | Yield of LEU (%) |
|---|---|---|---|---|
| 57 | 2 | 63.5 | 32.5 | 17 |
| 58 | 6 | 69 | 33.5 | 21 |

TABLE 16-continued

| Example | $NH_4Cl/Fe^{3+}$ (Molar ratio) | Conversion rate of AVLB (%) | Yield of VLB (%) | Yield of LEU (%) |
|---------|---|---|---|---|
| 59 | 8 | 77.5 | 35 | 21 |

Examples 60 to 61

The procedure was carried out in the same manner as in Example 56 except that $NH_4Cl$ in Example 56 was replaced by $(NH_4)_2SO_4$. The results are shown in Table 17.

TABLE 17

| Example | $(NH_4)_2SO_4/Fe^{3+}$ (Molar ratio) | Conversion rate of AVLB (%) | Yield of VLB (%) | Yield of LEU (%) |
|---------|---|---|---|---|
| 60 | 2 | 70.5 | 31.5 | 18 |
| 61 | 3 | 66 | 30 | 16 |

Example 62

In a 100 ml-reaction vessel equipped with a turning blade were places 19 mg of AVLB, 100 ml of $H_2O$, 0.2025 g of $FeCl_3.6H_2O$, 0.2162 g of $(NH_4)_2C_2O_4 \cdot H_2O$, 0.1604 g of $NH_4Cl$, 0.225 g of glycine, and 0.12 ml of 2N HCl. The mixture was stirred at 0° C. over 30 min. in a high speed with the turbine blade while air was bubbled. Then, 2 ml of an aqueous solution of $NaBH_4$ (0.227M) was dropped over ca. 1 min. By addition of 10 ml of 25% ammonia water, the solution was made basic followed by being extracted with 100 ml of ethyl acetate, 3 times. The following procedure was performed in the same manner as in Example 56. At this time, the conversion rate of AVLB was 80%, the yield of VLB was 41%, and the yield of LEU was 18%.

Examples 63 to 64

The procedure was carried out in the same manner as in Example 62 except that the amount of $FeCl_3.6H_2O$ in example 62 was varied. (The $(NH_4)_2C_2O_4/Fe^{3+}$, $NH_4Cl/Fe^{3+}$, and glycine/$Fe^{3+}$ ratios were identical with those of Example 62.) The results are shown in Table 18.

TABLE 18

| Example | $Fe^{3+}/AVLB$ (Molar ratio) | Conversion rate of AVLB (%) | Yield of VLB (%) | Yield of LEU (%) |
|---------|---|---|---|---|
| 63 | 42 | 77 | 39 | 19.5 |
| 64 | 16 | 86 | 33.5 | 14.5 |

Example 65

The procedure was carried out in the same manner as in Example 56 except that glycine in Example 56 was not added. At this time, the conversion rate of AVLB was 64%, the yield of VLB was 20%, and the yield of LEU was 16%.

Example 66

Following dissolving in 100 ml of water 19 mg of 3′,4′-anhydrovinblastine (AVLB), 32-fold molar excess $FeCl_3.6H_2O$ and 5-fold molar excess 2N HCl based on AVLB, 2-fold molar excess $(NH_4)_2C_2O_4$, 4-fold molar excess $NH_4Cl$ and 4-fold molar excess glycine, based on $Fe^{3+}$, air was bubbled over 30 min. at 0° C. This solution and a solution, which was prepared by dissolving 12.9 mg of $NaBH_4$ in 2 ml of water and cooling to 0° C., were introduced into a reaction column and were allowed to contact with each other. After the reaction was proceeded by passing the solution through the column for 1 min., the recation solution was introduced into aqueous ammonia (prepared by dilution of 2 ml of 25% aqueous ammonia with 5 ml of water).

This mixture was extracted with 100 ml of AcOEt, 3 times. The eluate was evaporated to dryness under reduced pressure at not higher than 40° C. The analysis of the procudt by high-performance liquid chromatography under the same conditions as in Example 17 showed that the conversion rate of AVLB was 67.5%, the yield of VLB was 32%, and the yield of LEU was 12%.

Example 67

The procedure was carried out in the same manner as in Example 66 except that AVLB was replaced by 21.2 mg of $AVLB \cdot H_2SO_1$ and 2N HCl was not added. At this time, the conversion rate of AVLB was 67%, the yield of VLB was 33.5%, and the yield of LEU was 13%.

Examples 68 to 71

The procedure was carried out in the same manner as in Example 66 except that the amount and concentration of $NaBH_4$ were varied. The results are shown in Table 19.

TABLE 19

| Example | $NaBH_4$ (mg/2 ml $H_2O$) | Conversion rate of AVLB (%) | Yield of VLB (%) | Yield of LEU (%) |
|---------|---|---|---|---|
| 68 | 17.2 | 83.5 | 36 | 13 |
| 69 | 25.8 | 78.5 | 34 | 14 |
| 70 | 34.4 | 86 | 36.5 | 19 |
| 71 | 43.0 | 84 | 36.5 | 15.5 |

Examples 72 to 73

The procedure was carried out in the same manner as in Example 67 except that twice the amount of $AVLB \cdot H_2SO_4$ was employed and the amount of $NaBH_4$ was varied. The results are shown in Table 20.

TABLE 20

| Example | $NaBH_4$ (mg/2 ml $H_2O$) | Conversion rate of AVLB (%) | Yield of VLB (%) | Yield of LEU (%) |
|---------|---|---|---|---|
| 72 | 17.2 | 56.5 | 27 | 10 |
| 73 | 34.4 | 69 | 34.5 | 15 |

Examples 74 to 75

The procedure was carried out in the same manner as in Example 66 except that the contact time was about 6 sec.; 38 mg of AVLB was employed; and the amount of $NaBH_4$ was veri ed. The results are shown in Table 21.

TABLE 21

| Example | $NaBH_4$ (mg/2 ml $H_2O$) | Conversion rate of AVLB (%) | Yield of VLB (%) | Yield of LEU (%) |
|---------|---|---|---|---|
| 74 | 25.8 | 70.5 | 28.5 | 11 |
| 75 | 34.4 | 76.5 | 33 | 14 |

Example 76

The procedure was carried out in the same manner as in Example 66 except that 38 mg of AVLB was employed; the amount of NaBH$_4$ was 34.4 mg; and the bubbling gas into the AVLB solution was changed to pure oxygen. At this time, the conversion rate of AVLB was 72.5%, the yield of VLB was 27.5%, and the yield of LEU was 11%.

Example 77

The procedure was carried out in the same manner as in Example 67 except that the amount of NaBH$_4$ was 34.4 mg, and that α, α'-bipyridine equivalent to the trivalent iron was added in place of NH$_4$Cl. At this time, the conversion rate of AVLB was 65%, the yield of VLB was 36%, and the yield of LEU was 9%.

Example 78

The procedure was carried out in the same manner as in Example 70 except that FeCl$_3$6H$_2$O, (NH$_4$)$_2$C$_2$O$_4$, NH$_4$Cl and glycine in the AVLB sulfate solution in Example 5 was prepared separately as 2 ml of an aqueous solution, and then three types of the solutions, i.e. this aqueous solution, AVLB sulfate solution, and NaBH$_4$ solution were simultaneously and continuously introduced into the column.

At this time, the conversion rate of AVLB was 80% the yield of VLB was 31%, and the yield of LEU was 12%.

Example 79

In a 300 ml-reaction vessel placed 100 ml of H$_2$O, 19 mg of AVLB 30-fold molar excess FeCl$_3$. 6H$_2$O, 5-molar excess 2N HCl and equivalent molar α,α'-bipyridyl, based on the anhydrovinblastine, 2-fold molar excess (NH$_4$)$_2$C$_2$O$_4$ based on the Fe$^{3+}$. The mixture was stirred over 30 min. under cooling in ice while air was bubbled. Following addition of 2 ml of an aqueous solution of NaBH$_4$ (0.227M), the mixture was stirred for an additional 30 min. Addition of 10 ml of 25 % ammonia water made the mixture basic. Then, the product was extracted with 100 ml of ethyl acetate, 3 times. The extracts were combined and evaporated to dryness under reduced pressure at 40° C. or less. The product was analyzed by high-performance liquid chromatography under the same conditions as in Example 17. At this time, the conversion rate of AVLB was 80%, the yield of VLB was 50% (selectively 63%), and the yield of LEU was 13%.

Example 80

The procedure was carried out in the same manner as in Example 79 except that α, α'-bipyridyl in Example 79 was not added. At this time, the conversion rate of AVLB was 92%, the yield of VLB was 44% (selectivity 48%), and the yield of LEU was 19%.

Example 81

The procedure was carried out in the manner as in Example 79 except that α, α'-bipyridyl in Example 79 was replaced by 4, 4'-dimenthy-2,2'-bipyridyl. At this time, the conversion rate of AVLB was 81%, the yield of VLB was 45% (selectivity 56%), and the yield of LEU was 17%.

Example 82

The procedure was carried out in the same manner as in Example 79 except that α, α'-bipyridyl was replaced by pyridine, and that the addition amount of pyridine was changed to 2.16 molar excess based on Fe$^{3+}$. At this time, the conversion rate of AVLB was 48%, the yield of VLB was 28% (selectivity 58%), and the yield of LEU was 4%.

Example 83

The procedure was carried out in the same manner as in Example 79 except that there was added 4-fold molar excedd glycine based on Fe$^{3+}$. At this time, the conversion rate of AVLB was 75%, the yield of VLB was 50% (selectivity 67 %), and the yield of LEU was 14%.

Comparative Example

To demonstrate increased yields, hence improved results, according to the process of the present invention using a large amount of water, the following comparative test was conducted using MeOH as a reaction medium.

To a 50 ml-reaction vessel were put 10 ml of MeOH, 1.9 mg of 3',4'-anhydrovinblastine (AVLB), and 1 ml of a MeOH solution of FeCl$_3$ (1.2M), and the mixture was stirred for 30 min. under cooling with ice, while air was bubbled. Following addition of 9 mg of NaBH$_4$, the mixture was stirred for additional 30 min. Then, 2 ml of 25% aqueous ammonia and 20 ml of water were added to make the solution basic. The products were extracted 3 times with 30 ml each of ethyl acetate. The extracts were combined and evaporated to dryness under reduced pressure at 40° or less. The resulting sample was analyzed by HPLC under the same condition of AVLB as well as less than 1% yield of vinblastine (VLB) and leurosidine (LEU) were obtained.

Compare the results obtained a total of VLB and LEU of in this comparative example of conversion of only 35% and a yield of less than 1% using a non-aqueous reaction medium, methanol, with the 95% conversion and 10% yield of VLB and 6% of LEU of Example 1.

We claim:
1. A process for the preparation of a compound represented by the formula (II):

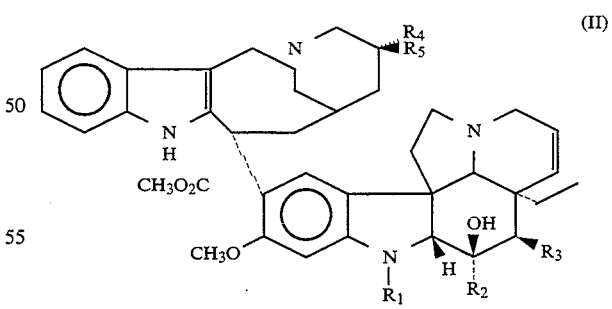

where R$_1$ represent a hydrogen atom a lower alkyl group or a formyl group; R$_2$ is a lower alkoxy-carbonyl group or CONH$_2$; R$_3$ is an acetoxy group or a hydroxy group; an R$_4$ is a hydroxy group and R$_5$ is an ethyl group, or R$_4$ is an ethyl group and R$_5$ is a hydroxy group, said process comprising the step of:

(1) dissolving, in an aqueous reaction medium containing from 80% by volume to 100% by volume of water, a compound of the formula (I):

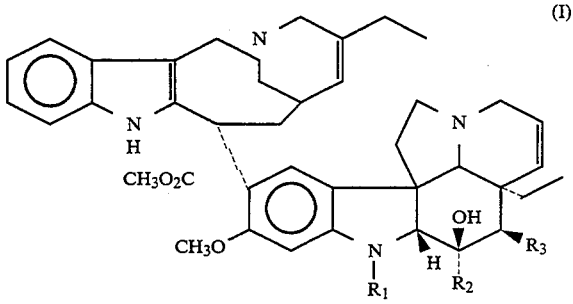

where $R_1$, $R_2$ and $R_3$ are as defined above, or salt thereof, oxalic acids ions, malonic acid ions or both, and a source of reactive trivalent iron soluble in the reaction medium selected from ferric chloride, ferric sulfate and ferric nitrate;

(2) dissolving oxygen in the reaction medium;

(3) adding to the oxygen-containing reaction medium a hydride source selected from sodium borohydride, potassium borohydride or sodium borocyanohydride; and thereafter (4) recovering the compound of formula (II) from the reaction medium.

2. A process for the preparation of a compound represented by the formula (II):

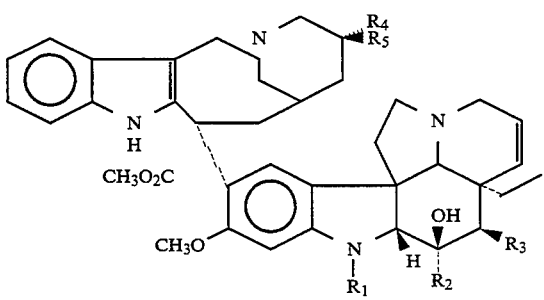

where $R_1$ represents a hydrogen atom, a lower alkyl group or a formyl group; $R_2$ is a lower alkoxy-carbonyl group of $CONH_2$, $R_3$ is an acetoxy group or a hydroxy group; and $R_4$ is a hydroxy group and $R_5$ is an ethyl group, or $R_4$ is and ethyl group and $R_5$ is a hydroxy group, said process comprising the steps of:

(1) dissolving, in an aqueous reaction medium containing 100% by volume of water, a compound of the formula (I):

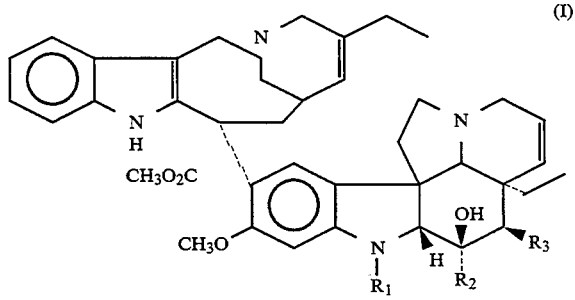

where $R_1$, $R_2$ and $R_3$ are as defined above, or a salt thereof, a source or reactive trivalent iron soluble in the reaction medium selected from ferric chloride, ferric sulfate and ferric nitrate;

(2) dissolving oxygen in the reactive medium;

(3) adding to the oxygen-containing reaction medium a hydride source selected from sodium borohydride, potassium borohydride or sodium borocyanohydride; and thereafter (4) recovering the compound of formula (II) from the reaction medium.

3. The process according to claim 1 wherein an inorganic anion source selected from ammonium chloride, ammonium bromide, ammonium sulfate, tetramethyl ammonium chloride or dimethyl ammonium chloride is added to the reaction medium prior to step (3).

4. The process of claim 2, wherein glycine or N-methylglycine is also added to the reaction medium prior to step (3).

5. The process according to claim 2 wherein an inorganic anion source selected from ammonium chloride, ammonium bromide, ammonium sulfate, tetramethyl ammonium chloride or dimethyl ammonia chloride is added to the reaction medium prior to step (3).

6. The process of claim 5 wherein glycine or N-methylglycine is also added to the reaction medium.

7. The process of claim 1, wherein glycine or N-methylglycine is also added to the reaction medium.

8. The process according to claim 3 wherein glycine or N-methylglycine is also added to the reaction medium.

9. The process according to claim 1, wherein pyridine, $\alpha\alpha'$-bipyridyl or 4,4-dimethyl-$\alpha\alpha'$-bipyridyl is added to the reaction mixture.

10. The process according to claim 9, wherein glycine or N-methylglycine is also added to the reaction medium.

11. The process according to claim 1, wherein maleic acid, succinic acid, itaconic acid, citraconic acid or ketosuccinic acid is also added to the reaction mixture.

12. The process of claim 11, wherein glycine or N-methylglycine is also added to the reaction mixture.

13. The process according to claim 1 or 2 wherein compound (II) is vinblastine.

14. The process according to claim 1 or 2 wherein compound (II) is leurosidine.

15. The process according to claim 1 or 2 wherein the respective components of the type (I) compound, a hydride source, oxygen, and trivalent iron source are contained in two or more solutions, and said two or more solutions are contacted with each other.

16. The process according to claim 15 wherein one or more components selected from an inorganic anion source, pyridine, alkylpyridine, $\alpha,\alpha'$-bipyridyl, or alkyl $\alpha,\alpha'$-bipyridyl a dicarboxylic acid or a salt thereof represented by the formula (III),

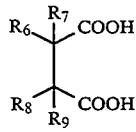

where $R_7$ and $R_9$ represent a hydrogen atom or a lower alkyl group; $R_6$ and $R_8$ represent a hydrogen atom or a lower alkyl group, or together form a double bond,
and glycine or N-methylglycine, are included in one or two solutions among two or more solutions to be contacted.

* * * * *